US008459095B2

(12) United States Patent
Morris et al.

(10) Patent No.: US 8,459,095 B2
(45) Date of Patent: Jun. 11, 2013

(54) PHANTOM FOR A QUANTITATIVE ULTRASOUND DEVICE

(75) Inventors: Richard Franklin Morris, Edgerton, WI (US); Steven Taylor Morris, Indianapolis, IN (US)

(73) Assignee: General Electric Company, Schenectady, NY (US)

( * ) Notice: Subject to any disclaimer, the term of this patent is extended or adjusted under 35 U.S.C. 154(b) by 644 days.

(21) Appl. No.: 12/570,563

(22) Filed: Sep. 30, 2009

(65) Prior Publication Data

US 2011/0076660 A1    Mar. 31, 2011

(51) Int. Cl.
    *G01D 18/00*    (2006.01)
(52) U.S. Cl.
    USPC .......................... 73/1.82; 434/274
(58) Field of Classification Search
    USPC .......................... 73/1.82; 434/274
    See application file for complete search history.

(56) References Cited

U.S. PATENT DOCUMENTS

| 4,286,455 | A  |   | 9/1981  | Ophir et al.    |         |
|-----------|----|---|---------|-----------------|---------|
| 5,625,137 | A  |   | 4/1997  | Madsen et al.   |         |
| 5,649,538 | A  | * | 7/1997  | Langton         | 600/437 |
| 5,670,719 | A  |   | 9/1997  | Madsen et al.   |         |
| 5,755,228 | A  |   | 5/1998  | Wilson et al.   |         |
| 6,264,607 | B1 |   | 7/2001  | Goll et al.     |         |
| 6,318,146 | B1 |   | 11/2001 | Madsen et al.   |         |
| 6,352,512 | B1 |   | 3/2002  | Wilson et al.   |         |
| 6,635,486 | B2 |   | 10/2003 | Madsen et al.   |         |
| 2004/0243003 | A1 |   | 12/2004 | Pasternak et al. |       |
| 2005/0075571 | A1 | * | 4/2005  | Barnes          | 600/459 |
| 2005/0141672 | A1 | * | 6/2005  | Endo et al.     | 378/207 |
| 2006/0079773 | A1 | * | 4/2006  | Mourad et al.   | 600/438 |

OTHER PUBLICATIONS

Clarke et al, A Phantom for Quantitative Ultrasound of Trabecular Bone, Phys. Med. Biol. 1677-1687 (1991).
Goldstein et al, Ethylene Glycol-Water Mixtures for use in Ultrasound Test Objects, J Clin. Ultrasound 7:465-470 (Dec. 1979).
Corsaro et al, A filled Silicone Rubber Materials System with Selectable Acoustic Properties for Molding and Coating Applications at Ultrasonic Frequencies, NRL Report 8301 (1979).
Ji, A Physical Model for Broadband Ultrasonic Studies of Cancellous Bone, PhD Thesis, University of Alberta (1998).

* cited by examiner

*Primary Examiner* — Hezron E Williams
*Assistant Examiner* — Gregory J Redmann
(74) *Attorney, Agent, or Firm* — Rathe Lindenbaum LLP

(57) ABSTRACT

A phantom for a quantitative ultrasound device is provided. The phantom includes a hollow casing, a first acoustic element disposed within the hollow casing, the first acoustic element simulating a broadband ultrasonic attenuation (BUA) of an exemplary bone; and a second acoustic element disposed within the hollow casing, the second acoustic element altering a speed of an ultrasonic signal transmitted through the phantom, the second acoustic element being disposed in-line with the first acoustic element. The phantom also includes a third acoustic element disposed within the hollow casing, the third acoustic element forming an acoustic coupling agent between the first acoustic element and the second acoustic element. A method of fabricating a phantom is also described herein.

30 Claims, 4 Drawing Sheets

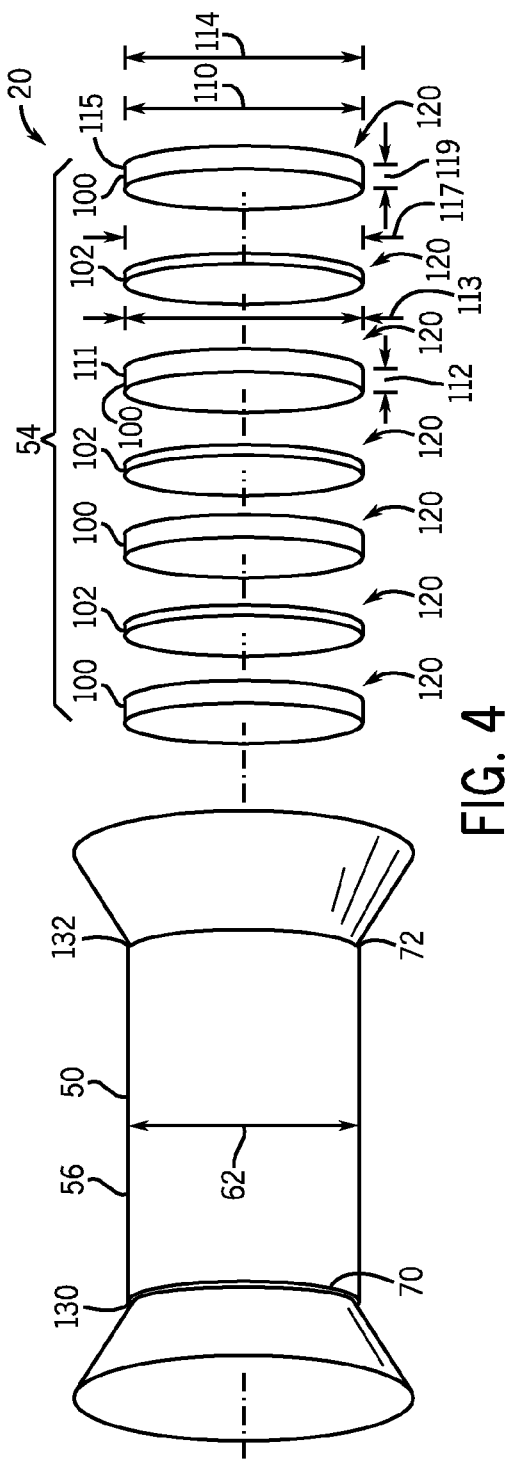
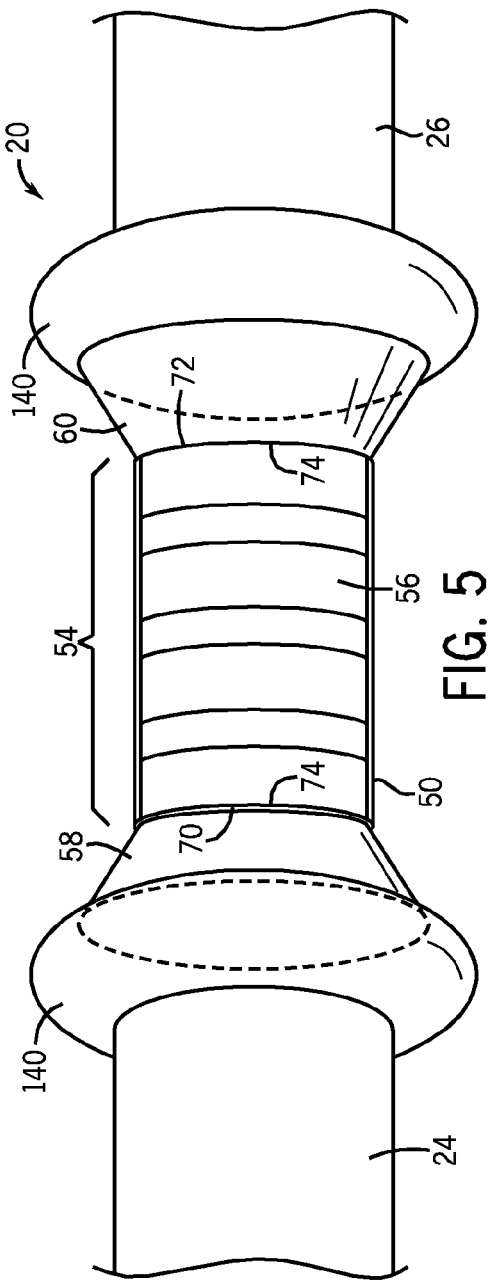
FIG. 4
FIG. 5

PHANTOM FOR A QUANTITATIVE ULTRASOUND DEVICE

BACKGROUND OF THE INVENTION

The subject matter disclosed herein relates generally to medical diagnostic systems, and more particularly to quantitative ultrasound (QUS) devices.

QUS devices such as ultrasonic densitometers and ultrasonometers use ultrasonic sound waves to measure bone integrity. Validation of QUS devices is an important function to ensure continued proper measurements that allow for proper diagnosis. QUS devices must remain stable for many years in order to properly assess the advancement of osteoporosis or monitor therapies. Thus, measurement parameters such as speed of sound (SOS), also referred to as time-of-flight, and broadband ultrasonic attenuation (BUA) need to be properly measured over time.

QUS phantoms are used to monitor QUS device stability. Conventional QUS phantoms use stable and well-characterized liquids such as water to attenuate signals. Other conventional QUS phantoms use a solid material such as rubber with known ultrasonic properties. Neither of these QUS phantoms satisfactorily simulates bone morphometry. Accordingly, the interaction of the acoustic wave from the QUS device and the phantom do not mimic bone, resulting in simulations that may not be particularly accurate. Additionally, liquids such as water are not very attenuative, such that the QUS device operates at minimum power. The solid phantoms also have aging effects. For example, materials with good BUA characteristics are typically rubbery. One typical material used for QUS phantoms is neoprene. As the neoprene material ages, more cross-linking between the molecules in the material occurs. This cross-linking results in a harder material and changes in the acoustic properties. The change in material hardness thereby reduces the utility of the QUS phantom for long term monitoring. Moreover, the water and solid QUS phantoms both have temperature induced drift or value changes.

BRIEF DESCRIPTION OF THE INVENTION

In accordance with one embodiment, a phantom for a quantitative ultrasound device is provided. The phantom includes a hollow casing, a first acoustic element disposed within the hollow casing, the first acoustic element simulating a broadband ultrasonic attenuation (BUA) of an exemplary bone; and a second acoustic element disposed within the hollow casing, the second acoustic element altering a speed of an ultrasonic signal transmitted through the phantom, the second acoustic element being disposed in-line with the first acoustic element.

In accordance with another embodiment, a phantom for a quantitative ultrasound device is provided. The phantom includes a hollow casing, a plurality of metallic acoustic elements disposed within the hollow casing, the metallic acoustic elements simulating a broadband ultrasonic attenuation (BUA) of an exemplary bone, a plurality of non-metallic acoustic elements disposed within the hollow casing, at least one of the plurality of non-metallic acoustic elements being disposed between a pair of metallic acoustic elements, the non-metallic acoustic elements being configured to alter a speed of an ultrasonic signal transmitted through the phantom, and a third acoustic element disposed within the hollow casing, the third acoustic element forming an acoustic coupling agent between the first acoustic element and the second acoustic element, the third acoustic element comprising a binary liquid mixture of glycol and water. In one preferred embodiment, the third acoustic element can be configured to compensate for temperature dependent changes of metallic and non-metallic elements.

In accordance with a further embodiment, a method of fabricating a phantom for a quantitative ultrasound device is provided. The method includes determining one or more acoustic properties of a bone to be mimicked, installing a first acoustic element within a hollow casing, the first acoustic element simulating a broadband ultrasonic attenuation (BUA) of the bone to be mimicked, and installing a second acoustic element within the hollow casing, the second acoustic element altering a speed of an ultrasonic signal transmitted through the phantom, the second acoustic element being disposed in-line with the first acoustic element.

BRIEF DESCRIPTION OF THE DRAWINGS

FIG. 4 is an exploded view of the phantom shown in FIGS. 2 and 3.

FIG. 5 is a pictorial illustration of the exemplary phantom shown in FIGS. 2-4 installed in an exemplary QUS device.

DETAILED DESCRIPTION OF THE INVENTION

Figure 1:
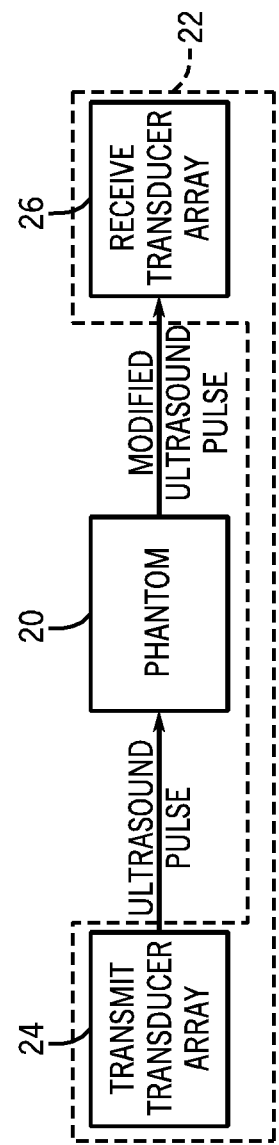
FIG. 1 is a simplified block diagram illustrating a phantom constructed in accordance with various embodiments for use with a Quantitative Ultrasound (QUS) device.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. One or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Exemplary embodiments of a phantom for use with a Quantitative Ultrasound (QUS) device, such as an ultrasound bone densitometer or ultrasonometer are described in detail below. Various embodiments provide a phantom that allows for modifying an ultrasound pulse between an ultrasound transmitter and an ultrasound receiver of a QUS device. The phantom mimics a bone. The phantom may be modified to mimic various bones. The phantom may be used in connection with any QUS device, for example, the Lunar Achillies ultrasonometer available from GE Healthcare or other ultrasound bone densitometer.

Specifically, as shown in FIG. 1, various embodiments of the invention provide a phantom 20 that is configured to mimic the properties or characteristics of bone, for example, the acoustic properties of a human heel bone (also referred to as the calcaneus). The phantom 20 may be used with a QUS device 22, for example, to validate or test the operation of the QUS device 22. In various embodiments, the QUS device 22 includes a transmit transducer array 24 and a receive transducer array 26 with the phantom 20 provided therebetween. More particularly, the phantom 20 is provided in an ultrasonic sound path between the transmit transducer array 24 and the receive transducer array 26. It should be noted that the transmit transducer array 24 and the receive transducer array 26 may include one or more transducer elements.

The transmission and reception of ultrasound pulses by the QUS device 22 are used to measure the physical properties of an object, for example, a bone of a human heel positioned between the transmit transducer array 24 and the receive transducer array 26. For example, the QUS device 22 is configured to measure the integrity and/or density of the object. In particular, the QUS device 22 can determine the physical properties and/or integrity of the object by comparing either relative transmit times (also referred to as time-of-flight or speed of sound) and/or relative broadband ultrasonic attenuation (BUA) through the object using the transmit transducer array 24 and the receive transducer array 26.

Accordingly, the phantom 20 in various embodiments mimics certain characteristics or properties, such as acoustic properties, of bone by altering or modifying an ultrasonic signal, which may be one or more pulses transmitted from the transmit transducer array 24. As a result of the modification of the signal, the receive transducer array 26 receives a signal that is modified with respect to, for example, time-of-flight or BUA. Because the signal is modified using a known value, the QUS device 22 can be tested for accuracy or validated when compared to the known value. Thus, the phantom 20 operates to modify the ultrasonic pulses used by the QUS device 22 to mimic a bone having a particular quality, characteristic or property, for example, a healthy bone or an osteoporotic bone. As an example, the time-of-flight or attenuation of an ultrasound pulse may be changed by altering the ultrasound pulse as the ultrasound pulse passes through the phantom 20 (as described in more detail herein) to generate a modified ultrasonic sound wave. The modified ultrasonic sound wave allows for a determination of whether the QUS device 22 measured an expected value for a particular bone density or integrity that the phantom 20 is mimicking.

Figure 2:
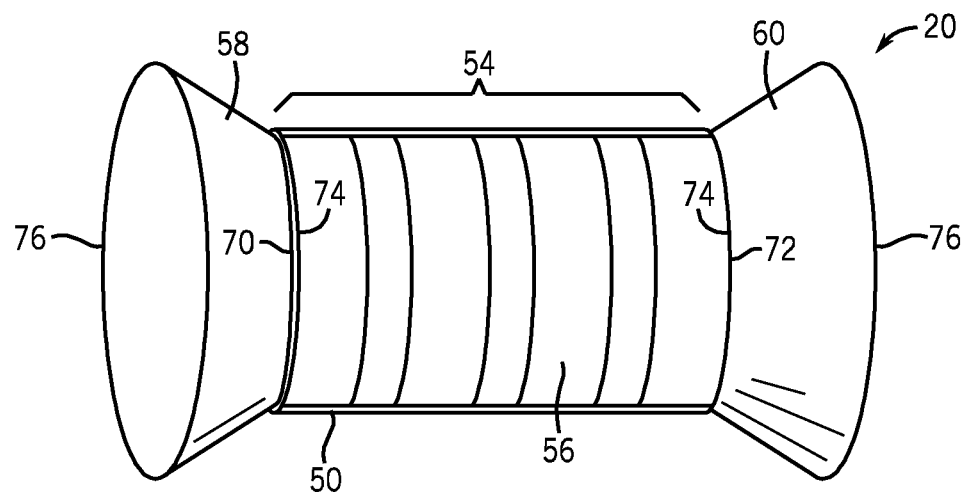
FIG. 2 is a pictorial illustration of an exemplary phantom constructed in accordance with various embodiments.
Figure 3:
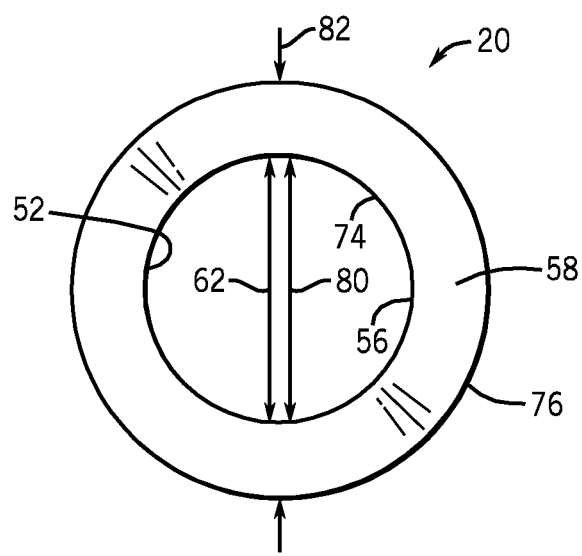
FIG. 3 is an end view of the phantom shown in FIG. 2.

FIG. 2 is a pictorial view of the exemplary phantom 20 shown in FIG. 1. FIG. 3 is an end view of the phantom 20 shown in FIG. 2. The phantom 20 as shown in FIG. 2 includes a cylindrical casing 50. The cylindrical casing 50 defines a hollow interior 52 that is configured to receive a plurality of acoustical elements 54 that simulate the human response of a predetermined bone to ultrasound. In the exemplary embodiment, the phantom 20 is configured to mimic the calcaneus bone of the human body. However, it should be realized that the acoustical elements 54 may be reconfigured to mimic the response of other bones imaged using the QUS device 22 described herein.

As shown in FIG. 2, the casing 50 includes a body portion 56 having a cylindrical shape and two hollow end portions 58 and 60 that are coupled to or form part of the body portion 56. The end portions 58 and 60 can be of any desired shape—such as, for example, flared outwards as representatively depicted, particularly as needed and/or desired for a given application. In the exemplary embodiment, the end portions 58 and 60 are formed unitarily with the body portion 56. Specifically, in the exemplary embodiment, the casing 50 is a single piece structure that includes both the body portion 56 and the two end portions 58 and 60. In the exemplary embodiment, the casing 50 is fabricated using a plastic material. Optionally, the casing 50 may be fabricated from other materials.

As shown in FIG. 3, the hollow interior 52 of the body portion 56 has a diameter 62. The diameter 62 is between approximately 1.75 inches and approximately 2.75 inches and approximately 2.0 inches. In the exemplary embodiment, the diameter 62 of the hollow interior 52 is between approximately 2.0 inches and approximately 2.5 inches. Referring again to FIG. 2, the body portion 56 includes a first end 70 and an opposing end 72. The first end 70 is coupled to, or formed unitarily with, the end portion 58 and the second end 72 is coupled to, or formed unitarily with, the end portion 60.

More specifically, each of the end portions 58 and 60 include a first end 74 that is coupled to, or formed unitarily with, the body portion first end 70 and/or second end 72, respectively. Each of the end portions 58 and 60 also includes a second end 76. In the exemplary embodiment, the first end 74 has a diameter 80 that is approximately equal to the inner diameter 60 of the body portion 56. Moreover, the second ends 76 each have a diameter 82 that is sized to enable an inflatable bladder to be received at least partially therein to secure the phantom 20 within the QUS device 22 during imaging as is discussed in more detail below.

FIG. 4 is an exploded view of the phantom 20 shown in FIGS. 2 and 3. As discussed above, the phantom 20 includes the plurality of acoustical elements 54 that are configured to simulate the human response of a predetermined bone to ultrasound. In the exemplary embodiment, the acoustical elements 54 are selected and arranged within the phantom body 50 to enable the QUS device 22 to accurately determine the physical properties and/or integrity of the phantom 20 by comparing either relative transmit times (also referred to as time-of-flight or speed of sound) and/or relative broadband ultrasonic attenuation (BUA) through the phantom 20 using the transmit transducer array 24 and the receive transducer array 26. More specifically, the QUS device 20 measures the ultrasound attenuation properties of the phantom 20 and uses the ultrasound attenuation properties as an indirect estimation of bone mineral density. As such, the size, thickness, and type of material disposed within the phantom 20 may be selected to mimic a healthy calcaneus bone or an osteoporotic calcaneus bone, or a range of bones between healthy and osteoporotic bones.

The plurality of acoustical elements 54 includes at least one metallic element 100 and at least one non-metallic element 102. In the exemplary embodiment, the acoustical elements 54 described herein are arranged to mimic a calcaneus bone and include a plurality of metallic elements 100 and a plurality of non-metallic elements 102. As shown in FIG. 4, a respective non-metallic element 102 is disposed between a pair of metallic elements 100. Optionally, a respective metallic element 100 is disposed between a pair of non-metallic elements 102. In the exemplary embodiment, the non-metallic elements 102 are disposed linearly or in-line with the metallic elements 100 such that ultrasound waves transmitted through the phantom 20 pass linearly through both the metallic elements 100 and the non-metallic elements 102.

The metallic element 100 is substantially disc-shaped and has an outer diameter 110 that, in the exemplary embodiment, is substantially similar to the inner diameter 62 of the body portion 56. In the exemplary embodiment, the phantom 20 includes a plurality of metallic elements 100. The plurality of metallic elements 100 may have the same outer diameter 62 or may have different outer diameters. For example, as shown in FIG. 4, a metallic element 111 may have an outer diameter 113 and a metallic element 115 may have an outer diameter 117. In one embodiment, the outer diameter 113 of the metallic element 111 is substantially the same as the outer diameter 117 of the metallic element 115. Optionally, the outer diameter 113 of the metallic element 111 is different than the same as the outer diameter 117 of the metallic element 115. In the exemplary embodiment, the outer diameter 110 of the metallic elements 100 is slightly less than the inner diameter 62 of the body portion 54 to enable the metallic elements 100 to be inserted into the body portion 54.

Each metallic element 110 also has a thickness 112. In the exemplary embodiment, the phantom 20 includes four metallic elements 100 each having a thickness 112 of approximately ½ inch to mimic a calcaneus bone. Optionally, at least one of the metallic elements 100 may have a different thickness. For example, as shown in FIG. 4, the metallic element 111 has a thickness 112 and metallic element 115 has a thickness 119. In one embodiment, the thickness 112 of the metallic element 111 is substantially the same as the thickness 119 of the metallic element 115. Optionally, the thickness 112 of the metallic element 111 is different than the thickness 119 of the metallic element 115. It should be realized that the diameters and thicknesses of the metallic elements 100 may be the same or different based on the bone being mimicked by the phantom 20

In the exemplary embodiment, the metallic element 100 is fabricated from a porous metallic material. For example, the metallic element 100 may be fabricated from an aluminum honeycomb material having a predetermined porosity. In the exemplary embodiment, the honeycomb material is an aluminum metal foam material having a large volume fraction of gas-filled pores. The foam material may be a closed-cell aluminum foam or an open-cell aluminum foam based on the bone to be mimicked.

The predetermined porosity of the metallic element 100 is selected such that the metallic element 100 mimics an exemplary spongy bone structure. Such exemplary bone structures may include a cancellous bone that is composed of dense collagenous tissue. One such example of an exemplary cancellous bone is the trabecula bone. During operation, the metallic elements 100 are configured to simulate the BUA over a clinically interesting human range. The range, and thus the quantity, size, and thickness of the metallic elements 100 is determined based on the human bone which the phantom 20 is configured to mimic. Moreover, the quantity, size, and thickness of the metallic elements 100 are also determined based on the condition, e.g. healthy or osteoporotic, human bone which the phantom 20 is configured to mimic.

The plurality of acoustical elements 54 also includes at least one non-metallic element 102. The non-metallic element 102 is substantially disc-shaped and has an outer diameter 114 that, in the exemplary embodiment, is substantially similar to the inner diameter 62 of the body portion 56 and substantially the same as the outer diameter 110 of the metallic elements 100. It should be realized that in the exemplary embodiment, the outer diameter 114 of the non-metallic element 102 is slightly less than the inner diameter 62 of the body portion 54 to enable the non-metallic element 102 to be inserted into the body portion 54. In the exemplary embodiment, the non-metallic element 102 is fabricated from a silicone rubber material. The non-metallic element 102 is configured to adjust the speed of sound (SOS) of the ultrasound beam such that the SOS through the phantom 20 substantially matches the BUA value for a particular bone condition, e.g. osteoporotic, normal, and/or above normal. More specifically, the non-metallic elements 102 are used to fine tune the speed of sound by decreasing the density of the phantom 20 such that the non-metallic elements 102 mimic the cortical bone. Therefore, it should be realized that the diameters and thicknesses of the non-metallic elements 100 may be the same or different within the phantom 20 based on the bone being mimicked by the phantom 20.

During operation, the metallic elements 100 are used to mimic the BUA of a healthy or osteoporotic bone. However, during operation, the speed of sound through the phantom 20 that does not include the non-metallic elements 102 is too fast and thus may exceed the clinically interesting range of human bones. Accordingly, the exemplary phantom 20 includes at least one non-metallic element 102 that functions as an acoustic damper to slow the sound waves and thus enable the phantom 20 to perform in the clinically interesting range of human bones. Specifically, sound travels faster through a non-healthy bone than a healthy bone. Therefore, in one embodiment, the thickness or quantity of non-metallic elements 102 may be increased to more closely mimic a healthy bone, e.g. increasing the thickness or quantity of non-metallic elements reduces the speed of sound through the phantom 20 thus more closely mimicking a healthy bone. Whereas, reducing the thickness or quantity of non-metallic elements 102 increases the speed of sound through the phantom 20 thus more closely mimicking a non-healthy or osteoporotic bone.

The plurality of acoustical elements 54 also includes a third acoustic element 120 that is configured to encapsulate both the metallic elements 100 and the non-metallic elements 102. More specifically, during assembly, a seal 130 is installed proximate to the body portion first end 70. The metallic elements 100 and the non-metallic elements 102 are then inserted into the body portion 56 of the casing 50. The remaining portion of the body portion 56 is then filled with the third acoustic element 120 and a second seal 132 is installed proximate to the body portion second end 72. The seals 130 and 132 secure the metallic elements 100 and the non-metallic elements 102 within the body portion 56 and also prevent the third acoustical element 120, in various embodiments, from leaking from the body portion 56.

In the exemplary embodiment, the third acoustic element 120 encapsulates both the metallic elements 100 and the non-metallic elements 102 by filling any voids within the casing 50. The third acoustic element 120 also forms an acoustic coupling agent between the metallic elements 100 and the non-metallic elements 102. Moreover, the third acoustic element 120 is also configured to compensate for any temperature dependent changes of the metallic elements 100 and the non-metallic elements 102. In the exemplary embodiment, the third acoustic element 120 is a liquid binary mixture that includes both glycol and water. Optionally, the third acoustic element 120 may include any liquid material that exhibits good long-term acoustic stability.

In some embodiments, the phantom 20 as shown in FIGS. 2-4 is provided. The phantom 20 includes the plurality of acoustic elements 54 housed in the casing 50. In various embodiments, such as FIG. 5, for example, the phantom 20 is positioned such that when placed within the QUS device 22, a pair of bladders 140 secure the phantom 20 between the transmit transducer array 24 and the receive transducer array 26. More specifically, to position the phantom 20 within the QUS device 22, the pair of bladders 140 are inflated such that each bladder 140 extends at least partially into one of the, preferably cone-shaped, end portions 58 and 60, respectively. It should be noted that bladders 140, which are inflatable, may also have an acoustic coupling fluid disposed therein to improve the acoustic coupling between the transmit transducer array 24, the phantom 20, and the receive transducer array 26.

It also should be noted that although the casing 50 includes one or more, again preferably cone-shaped in at least one embodiment, end portions 58 and 60 to receive a respective bladder 140, the casing 50 and the end portions 58 and 60 may also be otherwise shaped and sized as needed and/or desired. For example, the casing 50 may be shaped and sized to fit within a particular QUS device 22. Additionally, the casing 50 may be shaped and sized such that the phantom 20 fits within certain QUS devices 22, while not fitting within other QUS devices 22.

The various components of the phantom 20 may be modified or configured to mimic a certain type of bone or certain properties of a bone, such as certain acoustic properties as described herein. In some embodiments, the phantom 20 includes three different acoustic elements 52. The three different acoustic elements 54 include a metallic element 100, a non-metallic element 102, and a fluid element 120. The combination of the three types of acoustic elements 54 enables the phantom 20 to mimic the speed of sound and the DUA and attenuation of the sound wave for a specific bone of a human body. The combination of the acoustic elements 54 may be adjusted or fine-tuned to make the phantom 20 stable over a predetermined temperature range. The phantom 20 described herein includes several types of solid materials and a liquid material that in combination make the phantom 20 stable over a longer period of time and over larger temperature variations. The diameter, quantity, and/or thickness of the solid acoustic materials may be modified to enable the phantom 20 to more accurately mimic a specific human bone. For example, the diameter, quantity, and/or thickness of each of the solid acoustic materials 100 and 102 installed in the single phantom 20 are selected to cover the human possible measurement range and mimic human acoustic properties. By modifying the properties of the metallic elements and/or the non-metallic elements 102, the phantom 20 may be adjusted to increase or reduce the speed of sound through the phantom 20 and thereby mimic a specific acoustical property of particularly the foot including the bone and the tissue that surrounds the bone.

Figure 6:
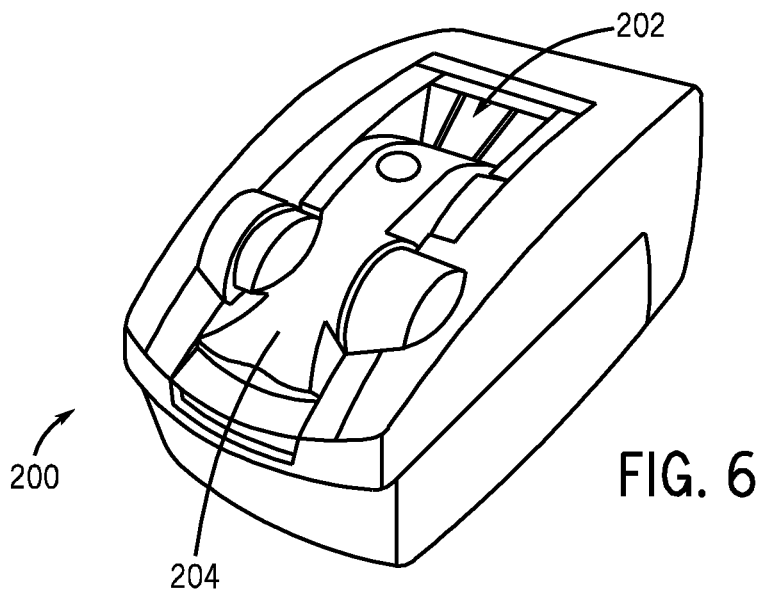
FIG. 6 is a perspective view of a QUS device in connection with which a phantom in accordance with various embodiments may be used.
Figure 7:
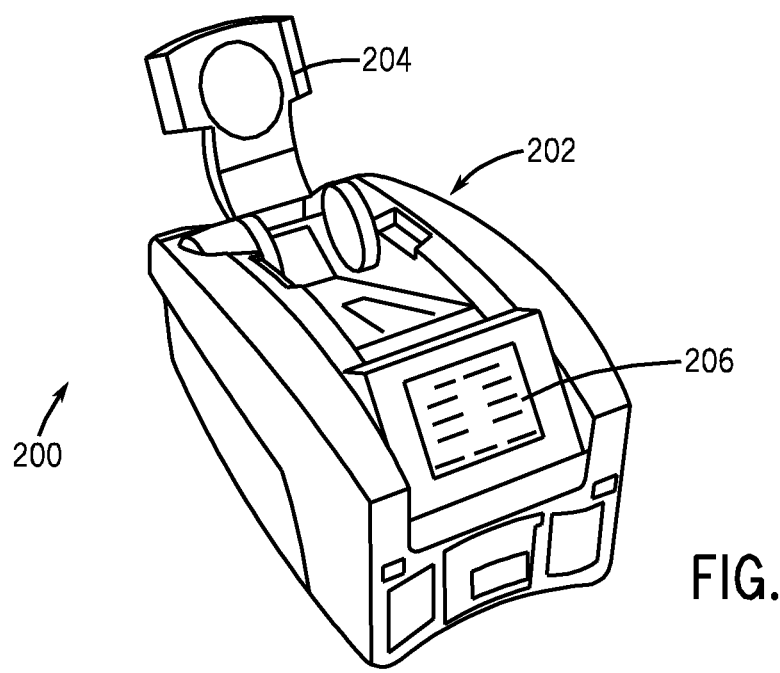
FIG. 7 is another perspective view of a QUS device in connection with which a phantom in accordance with various embodiments may be used.

The various embodiments may be used to provide a phantom for use with any type of QUS device and to simulate different bones or portions of the body. For example, as shown in FIGS. 6 and 7 the QUS device may be an ultrasonometer 200 having a receiving portion 202 configured to receive therein a heel and a support member 204 for supporting a back of a leg. A display 206 also may be provided. The ultrasonometer 200 may be for example, an Achilles ultrasonometer with the various embodiments of phantoms described herein inserted within the receiving portion 202 and operating to modify ultrasound pulses transmitted therein to mimic a heel.

Thus, various embodiments of the invention provide a phantom that simulates acoustic properties of bones, for example, by varying one or more time-of-flight and BUA values approximating, for example, a human heel bone. The simulated properties provide acoustic characteristics similar to bone. It should be noted that in some embodiments the simulated properties may be adjusted by modifying the size and/or shape of the metallic element 100 and/or non-metallic elements 102. In other embodiments, various types of bone quality may be simulated by increasing or decreasing the quantity of metallic element 100 and/or non-metallic elements 102 within the phantom 20.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A phantom for a quantitative ultrasound device, the phantom comprising:
   a hollow casing;
   a first acoustic element disposed within the hollow casing, the first acoustic element simulating a broadband ultrasonic attenuation (BUA) of an exemplary bone; and
   a second non-metallic acoustic element disposed within the hollow casing, the second acoustic element configured to alter a speed of an ultrasonic signal transmitted through the phantom, the second acoustic element being disposed in-line with the first acoustic element.

2. A phantom in accordance with claim 1 further comprising a third acoustic element disposed within the hollow casing, the third acoustic element forming an acoustic coupling agent between the first acoustic element and the second acoustic element.

3. A phantom in accordance with claim 1 further comprising a plurality of first acoustic elements and a plurality of second acoustic elements, the first acoustic elements being interleaved with the second acoustic elements.

4. A phantom in accordance with claim 1 wherein the first acoustic element comprises an aluminum disc.

5. A phantom in accordance with claim 1 wherein the first acoustic element comprises an aluminum honeycomb material having a predetermined porosity selected to mimic a human bone.

6. A phantom in accordance with claim 1 wherein the second acoustic element comprises a rubber material.

7. A phantom in accordance with claim 1 wherein the second acoustic element comprises a silicone rubber disc.

8. A phantom in accordance with claim 1 further comprising a plurality of second acoustic elements, the quantity of second acoustic elements being selected to substantially match a BUA of the first acoustic element.

9. A phantom in accordance with claim 1 further comprising a third acoustic element disposed within the hollow casing, the third acoustic element including a binary liquid mixture including glycol and water.

10. A phantom in accordance with claim 1 wherein the first and second elements are configured to mimic a calcaneus bone.

11. A phantom in accordance with claim 1 wherein the hollow casing comprises a pair of cone-shaped end portions, each cone-shaped end portion configured to receive an inflatable bladder at least partially therein.

12. A phantom in accordance with claim 1 wherein the first and second acoustic elements have an outer diameter that is substantially similar to an inner diameter of the a hollow casing, the first and second acoustic elements being sized to fit into the hollow casing.

13. A phantom in accordance with claim 1 wherein the first acoustic element has an outer diameter that is greater than an outer diameter of the second acoustic element.

14. A phantom in accordance with claim 1 wherein the first and second acoustic elements are configured to alter the attenuation of a sound wave transmitted through the phantom to mimic the attenuation of a bone of a human heel.

15. A phantom in accordance with claim 1 wherein the first and second acoustic materials are configured to change one of a time-of-flight and a BUA of a received ultrasonic signal to generate a modified ultrasonic sound wave that mimics a human bone.

16. A phantom for a quantitative ultrasound device, the phantom comprising:
a hollow casing;
a plurality of metallic acoustic elements disposed within the hollow casing, the metallic acoustic elements simulating a broadband ultrasonic attenuation (BUA) of an exemplary bone;
a plurality of non-metallic acoustic elements disposed within the hollow casing, at least one of the plurality of non-metallic acoustic elements being disposed between a pair of metallic acoustic elements, the non-metallic acoustic elements being configured to alter a speed of an ultrasonic signal transmitted through the phantom; and
a third acoustic element disposed within the hollow casing, the third acoustic element forming an acoustic coupling agent between the first acoustic element and the second acoustic element.

17. A phantom for a quantitative ultrasound device, the phantom comprising:
a hollow casing;
a first acoustic element disposed within the hollow casing, the first acoustic element simulating a broadband ultrasonic attenuation (BUA) of an exemplary bone, wherein the first acoustic element comprises a porous metallic material having a predetermined porosity selected to mimic a human bone; and
a second acoustic element disposed within the hollow casing, the second acoustic element configured to alter a speed of an ultrasonic signal transmitted through the phantom, the second acoustic element being disposed in-line with the first acoustic element.

18. The phantom in accordance with claim 17, wherein the porous metallic material comprises an aluminum honeycomb material.

19. A phantom for a quantitative ultrasound device, the phantom comprising:
a hollow casing comprising a pair of cone-shaped end portions, each cone-shaped end portion configured to receive an inflatable bladder at least partially therein;
a first acoustic element disposed within the hollow casing, the first acoustic element simulating a broadband ultrasonic attenuation (BUA) of an exemplary bone; and
a second acoustic element disposed within the hollow casing, the second acoustic element configured to alter a speed of an ultrasonic signal transmitted through the phantom, the second acoustic element being disposed in-line with the first acoustic element.

20. A phantom for a quantitative ultrasound device, the phantom comprising:
a hollow casing;
a first acoustic element disposed within the hollow casing, the first acoustic element simulating a broadband ultrasonic attenuation (BUA) of an exemplary bone; and
a second acoustic element disposed within the hollow casing, the second acoustic element configured to alter a speed of an ultrasonic signal transmitted through the phantom, the second acoustic element being disposed in-line with the first acoustic element, wherein the first and second acoustic elements have an outer diameter that is substantially similar to an inner diameter of the a hollow casing, the first and second acoustic elements being sized to fit into the hollow casing.

21. A phantom in accordance with claim 20, wherein the first acoustic element has an outer diameter that is greater than an outer diameter of the second acoustic element.

22. A phantom in accordance with claim 20 further comprising a liquid within the hollow casing between the first acoustic element and the second acoustic element.

23. The phantom of claim 16, wherein the third acoustic element comprises a liquid.

24. The phantom of claim 16, wherein the third acoustic element comprises a binary liquid mixture of glycol and water.

25. The phantom of claim 16, wherein the third acoustic element encapsulates the plurality of metallic acoustic elements and the plurality of non-metallic acoustic elements.

26. The phantom of claim 16, wherein the third acoustic element is configured to compensate for temperature dependent changes of the plurality of metallic acoustic elements and the plurality of non-metallic acoustic elements.

27. The phantom of claim 16, wherein the plurality of metallic acoustic elements comprises a first metallic acoustic element having a first thickness and a second metallic acoustic element having a second thickness different than the first thickness.

28. A phantom for a quantitative ultrasound device, the phantom comprising:
a hollow casing;

a plurality of first acoustic elements disposed within the hollow casing, the plurality of first acoustic elements simulating a broadband ultrasonic attenuation (BUA) of an exemplary bone; and a plurality of second acoustic elements disposed within the hollow casing, the plurality of second acoustic elements configured to alter a speed of an ultrasonic signal transmitted through the phantom, the plurality of second acoustic elements being disposed in-line with the plurality of first acoustic elements.

29. The phantom of claim 28, wherein the plurality of first acoustic elements are interleaved with the plurality of second acoustic elements.

30. The phantom of claim 28 further comprising a third liquid acoustic element disposed within the hollow casing and forming an acoustic coupling agent between the first plurality of acoustic elements and the second plurality of acoustic elements.

* * * * *